United States Patent [19]

Yazawa et al.

[11] Patent Number: 5,801,178
[45] Date of Patent: Sep. 1, 1998

[54] ANILINE DERIVATIVE HAVING POLYUNSATURATED FATTY ACID RESIDUE AND USE THEREOF

[75] Inventors: Kazunaga Yazawa; Kazuo Watanabe; Yasuharu Ijuin. all of Sagamihara; Mayumi Shikano. Machida; Yasuji Soda. Kobe; Tetsuya Kosaka. Ibaraki; Naoto Matsuyama. Takatsuki; Koji Mizuno. Kyoto. all of Japan

[73] Assignees: Nippon Shoji Kaish Ltd.. Osaka; Sagami Chemical Research. Kanagawa, both of Japan

[21] Appl. No.: 597,983

[22] Filed: Feb. 7, 1996

[30] Foreign Application Priority Data

Feb. 8, 1995 [JP] Japan ................... 7-020741

[51] Int. Cl.$^6$ ............... A61K 31/495; A61K 31/165; C07C 233/09; C07D 295/185
[52] U.S. Cl. ............... 514/255; 514/596; 514/598; 514/627; 544/388; 554/35; 554/56; 554/58; 554/62; 554/65; 554/67
[58] Field of Search ............... 544/388; 514/255, 514/596, 598, 627; 554/35, 56, 58, 62, 65, 67

[56] References Cited

U.S. PATENT DOCUMENTS

| | | | |
|---|---|---|---|
| 3,995,059 | 11/1976 | Fukumaru et al. | 554/35 |
| 4,053,509 | 10/1977 | Faro et al. | 554/65 |
| 4,655,973 | 4/1987 | Yamatsu et al. | 554/35 |
| 4,716,175 | 12/1987 | Hoefle et al. | 514/357 |
| 4,751,026 | 6/1988 | Hoefle et al. | 554/65 |
| 5,254,590 | 10/1993 | Malen et al. | 554/35 |

OTHER PUBLICATIONS

Roth et al., Inhibitors of Acyl–CoA:Cholesterol Acyltransferase. 1. Identification and Structure–Activity Relationships of a Novel Series of Fatty Acid Anilide Hypocholesterolemic Agents; *J. Med. Chem.* 1992, 35, 1609–1617.
Protein, Nucleic Acid and Enzyme. vol. 39, No. 9, 1532–1547 (1994) (Article Not Translated).

Roark et al.. Inhibitors of Acyl–CoA: Cholesterol Acyltransferase (ACAT). 2. Modification of Fatty Acid Anilide ACAT Inhibitors: Bioisosteric Replacement of the Amide Bond. *Journal of Medicinal Chemistry,* vol. 36, No. 11, May 28, 1993, pp. 1662–1668.

*Primary Examiner*—Emily Bernhardt
*Attorney, Agent, or Firm*—Leydig, Voit & Mayer, Ltd.

[57] ABSTRACT

An aniline derivative of the formula (1)

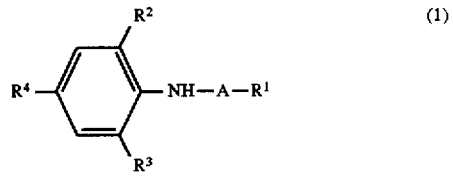

wherein $R^1$ is an eicosapentaenoyl or docosahexaenoyl; $R^2$ and $R^3$ are each independently an alkyl or alkoxy having 1 to 6 carbon atoms, or a halogen atom; $R^4$ is a hydrogen atom, an alkyl or alkoxy having 1 to 6 carbon atoms, or a halogen atom; and A is a single bond, —C(=O)NH—$(CH_2)_n$—NH— wherein n is 2 or 3, or a bivalent group of the following formula

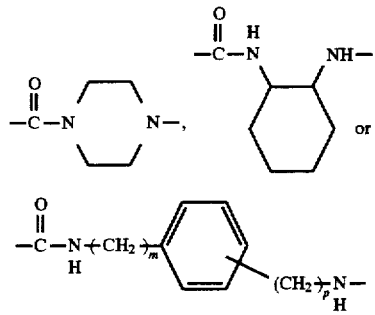

wherein m and p are each independently 0 or 1. The aniline derivative of the present invention has high inhibitory activity against and high selectivity for ACAT derived from macrophage and is useful as an agent for the prophylaxis and treatment of arteriosclerosis.

5 Claims, No Drawings

ANILINE DERIVATIVE HAVING POLYUNSATURATED FATTY ACID RESIDUE AND USE THEREOF

FIELD OF THE INVENTION

The present invention relates to novel aniline derivatives having a polyunsaturated fatty acid residue, which show inhibitory activity against acyl CoA:cholesterol acyltransferase (hereinafter abbreviated as ACAT), ACAT inhibitors containing said derivatives, and agents for the prophylaxis and treatment of arteriosclerosis, which contain said derivatives.

BACKGROUND OF THE INVENTION

ACAT is a membrane-bound enzyme which is mostly present in intracellular microsomal fractions and acts on cholesterol to catalyze formation of an ester type cholesterol, i.e., cholesteryl ester. Its physiological significance varies depending on the organ and cells in which ACAT is present.

In macrophages, for example, ACAT catalyzes formation of an ester type cholesterol which accumulates in the cells to induce foaming of the cells, which being an initial lesion of arteriosclerosis. In intestinal epithelial cells, ACAT catalyzes re-esterification of a dietary cholesterol taken into the cells, and acts as a rate limiting factor of cholesterol absorption. In the liver, it concerns the storage of cholesterol as a precursor of a bile acid, and also forms an ester type cholesterol in very low density lipoproteins (VLDL), as well as reserved cholesterol.

From the viewpoints of the prophylaxis and treatment of arteriosclerosis, it is desired to highly and selectively inhibit ACAT present in macrophages, which directly forms the lesion of arteriosclerosis.

There have been heretofore known various amide compounds, urea compounds and imidazole compounds as ACAT inhibitors [Hiroshi Tomoda, Protein, Nucleic Acid and Enzyme, vol. 39, No. 9, 1532–1547 (1994)]. It has been also known that long chain fatty acid anilide compounds have ACAT-inhibitory activity [EP-A-0242610, U.S. Pat. No. 4,716,175, J. Med. Chem., 35, 1609–1617 (1992)].

The above-mentioned compounds are not necessarily satisfactory in terms of the selectivity for ACAT derived from macrophage.

It is therefore an object of the present invention to provide a novel compound having high selectivity for and high inhibitory activity against ACAT derived from macrophage, and novel ACAT inhibitors and agents for the prophylaxis and treatment of arteriosclerosis, both containing said compound.

SUMMARY OF THE INVENTION

According to the present invention, there are now provided aniline derivatives which have a certain polysaturated fatty acid residue, and superior inhibitory activity and selectivity.

That is, the present invention provides aniline derivatives of the formula (1)

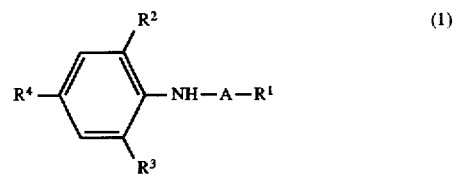

wherein $R^1$ is an eicosapentaenoyl or docosahexaenoyl;

$R^2$ and $R^3$ are each independently an alkyl or alkoxy having 1 to 6 carbon atoms, or a halogen atom;

$R^4$ is a hydrogen atom, an alkyl or alkoxy having 1 to 6 carbon atoms, or a halogen atom; and A is a single bond, —C(=O)NH—$(CH_2)_n$—NH— wherein n is 2 or 3, or a bivalent group of the following formula

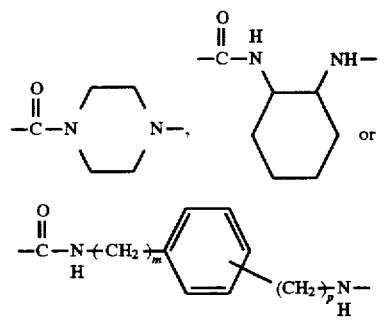

wherein m and p are each independently 0 or 1, and pharmaceutical compositions, ACAT inhibitors and agents for the prophylaxis and treatment of arteriosclerosis containing the derivative as an active ingredient.

DETAILED DESCRIPTION OF THE INVENTION

As used herein, alkyl having 1 to 6 carbon atoms may be linear, branched or cyclic, and is exemplified by methyl, ethyl, n-propyl, isopropyl, n-butyl, isobutyl, sec-butyl, tert-butyl, n-pentyl, isopentyl, neopentyl, tert-pentyl, hexyl, cyclopentyl and cyclohexyl, with preference given to methyl, ethyl and isopropyl. Alkoxy having 1 to 6 carbon atoms may be linear, branched or cyclic, and is exemplified by methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, hexyloxy, cyclopentyloxy and cyclohexyloxy, with preference given to methoxy. Halogen atom may be, for example, fluorine atom, chlorine atom, bromine atom or iodine atom, with preference given to fluorine atom.

The preferable compounds of the present invention are those of the formula (1) wherein $R^1$ is 5,8,11,14,17-eicosapentaenoyl or 4,7,10,13,16,19-docosahexaenoyl, $R^2$ and $R^3$ are each independently methyl, ethyl, isopropyl, methoxy or fluorine atom, $R^4$ is a hydrogen atom, methyl, methoxy or fluorine atom, and A is a single bond, —C(=O)NH—$(CH_2)_2$—NH— or a bivalent group of the formula

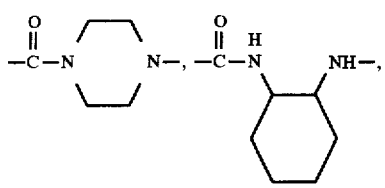

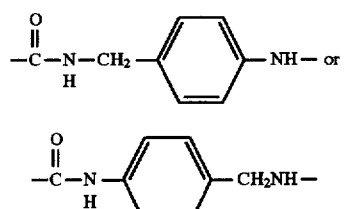

From the aspect of high inhibitory activity, $R^4$ is particularly preferably a hydrogen atom.

The aniline derivatives of the above-mentioned formula (1) can be produced from a polyunsaturated fatty acid by a method shown in the following reaction scheme.

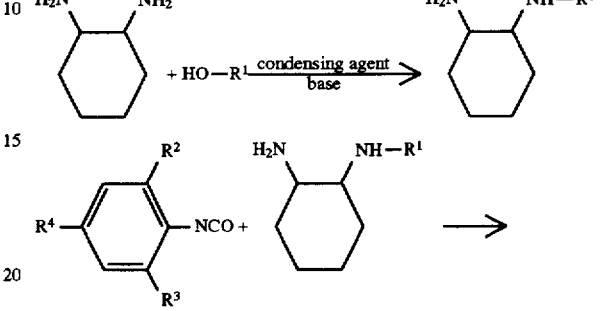

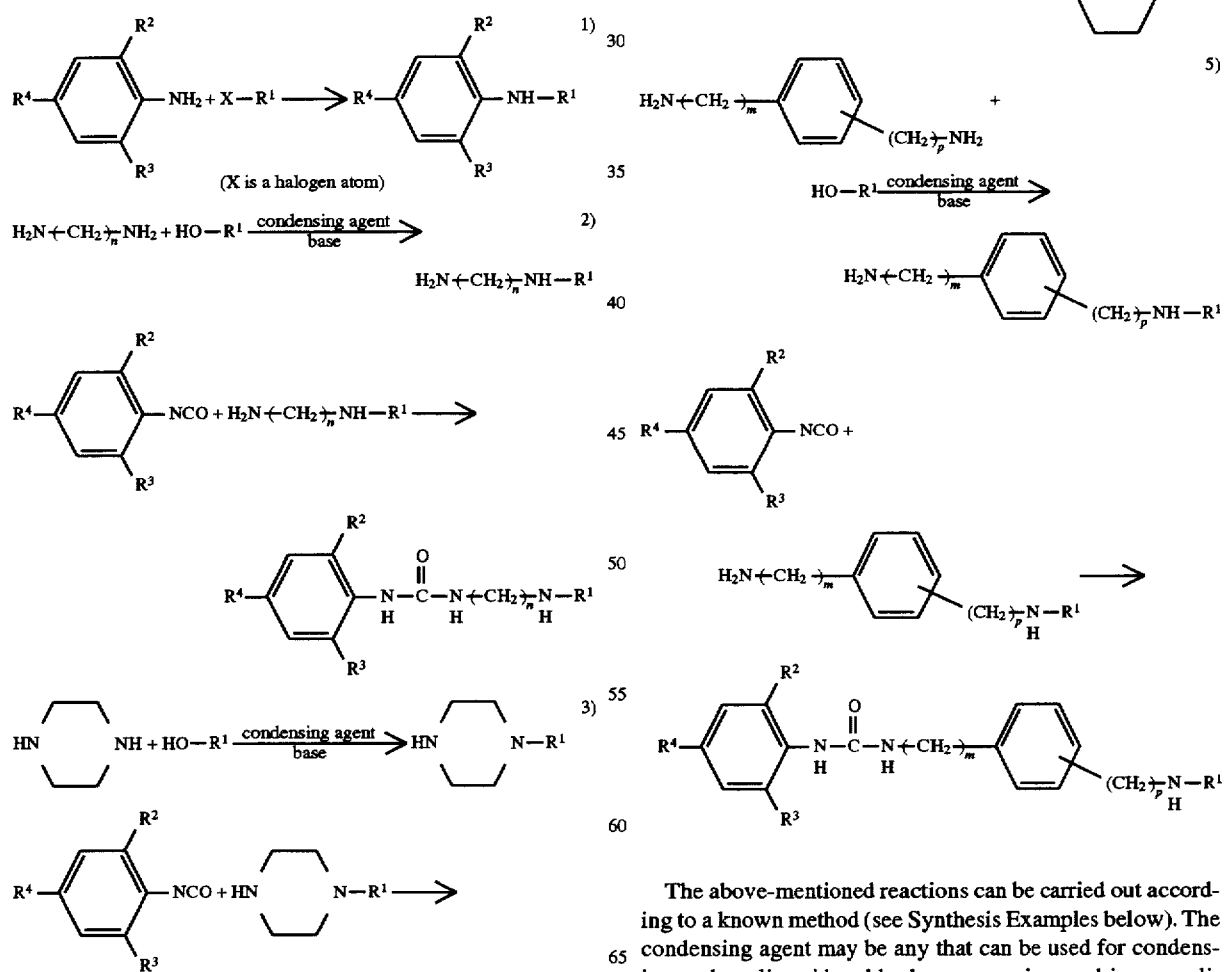

The above-mentioned reactions can be carried out according to a known method (see Synthesis Examples below). The condensing agent may be any that can be used for condensing carboxylic acid and hydroxy or amino, and is exemplified by dicyclohexylcarbodiimide (DCC) and N,N'- carbonyldiimidazole (CDI). As the base, organic amines such as triethylamine and pyridine are preferably used.

The ACAT inhibitor containing the above compounds of the present invention as an active ingredient can be applied by oral administration, parenteral administration (e.g., subcutaneous, intravenous, intramuscular and sternal injections), intrarectal administration and the like. While the doses of the above-mentioned compounds vary depending on the symptom and age of patients, administration route and the like, they are generally about 0.01–500 mg/kg/day. The above compounds can be administered as they are, but they are generally formulated into preparations before use. For formulation into preparations, pharmacologically and pharmaceutically acceptable ingredients such as conventional diluents, carriers, extenders and additives are used according to the method generally employed in this field. The preparations may be made into sustained release preparations by a known method. Examples of the dosage form include tablets, granules, fine particles, powders, capsules, syrups, elixirs, injections, eye drops, ophthalmic ointments and suppositories. The active ingredient is contained in the preparations in a proportion of about 0.01–99.99%, preferably about 5–70%.

The aforesaid ingredients are appropriately selected according to the administration route, such as oral administration (oral preparation), injection (preparations for injection), mucosal administration (e.g., buccal, troche and suppository) and external administration (e.g., ointment and plaster). For example, excipients (e.g., starch, lactose, crystalline cellulose, calcium lactate, magnesium aluminometasilicate and anhydrous silicate), disintegrators (e.g., carboxymethylcellulose and calcium carboxymethylcellulose), lubricants (e.g., magnesium stearate and talc), coating agents (e.g., hydroxyethylcellulose), and flavoring agents are used for oral agents and mucosal agents; solubilizers and auxiliary solubilizers capable of forming aqueous injections (e.g., distilled water for injection, physiological saline and propylene glycol), suspending agents (e.g., surfactant such as polysorbate 80), pH regulators (e.g., organic acid and metal salt thereof) and stabilizers are used for injections; and aqueous or oily solubilizers and auxiliary solubilizers (e.g., alcohols and fatty acid esters), tackifiers (e.g., carboxy vinyl polymer and polysaccharides) and emulsifiers (e.g., surfactant) are used for external agents.

These preparations can be produced according to the method described in, for example, Japan Pharmacopoeia, 10th ed., General Rules for Preparations or an appropriate modification thereof.

The present invention is explained in more detail by illustrative Synthesis Examples and Experimental Examples, to which the present invention is not limited.

Synthesis Example 1

Synthesis of N-(2,4,6-trimethoxyphenyl)-5,8,11,14, 17-eicosapentaenamide (Compound 1)

Eicosapentaenoic acid (EPA, 95%, 1.21 g, 4 mmol) and oxalyl chloride (0.761 g, 6 mmol) were dissolved in chloroform and the mixture was reacted for about 2 hours while cooling in a nitrogen stream. The mixture was concentrated under reduced pressure and anhydrous tetrahydrofuran (THF, 5 ml) was added for dissolution. This solution was added to a solution of 2,4,6-trimethoxyaniline (732.8 mg, 4 mmol) and triethylamine ($Et_3N$, 405 mg, 4 mmol) dissolved in anhydrous tetrahydrofuran (3 ml), and the mixture was reacted overnight under cooling in a nitrogen stream. The resulting precipitate was filtered off and the obtained filtrate was concentrated under reduced pressure. The concentrate was dissolved in ethyl acetate (AcOEt, 120 ml) and the AcOEt layer was washed with 2N hydrochloric acid (30 ml) and saturated brine, which was followed by concentration under reduced pressure of the obtained AcOEt layer. The concentrate was applied to a silica gel ($SiO_2$, 60 g) column previously activated with hexane and eluted successively with hexane (500 ml), hexane-AcOEt (8:2, 500 ml), hexane-AcOEt (7:3, 500 ml) and hexane-AcOEt (6:4, 1,000 ml). The objective fractions were recovered from the obtained eluate fractions based on thin-layer chromatography (TLC) analysis as an index. The fractions obtained were concentrated to give the objective compound (732 mg, yield 94%). As a result of the TLC analysis [silica gel plate, developing solvent:hexane-AcOEt (6:4)], this compound showed a single spot by the detection with iodine and ultraviolet irradiation.

EI-MS (m/z): 467 ($M^+$)

$^1$H-NMR (400 MHz, $CDCl_3$): δ0.97 (t, J=7.5 Hz, 3H), 1.82 (m, J=6.6 Hz, 2H), 2.07 (q, J=7.5 Hz, 2H), 2.20 (m, J=6.0 Hz, 2H), 2.38 (t, J=6.6 Hz, 2H), 2.84 (m, 8H), 3.8 (s, 9H), 5.38 (m, 10H), 6.14 (s, 2H), 6.40 (bs, 1H).

$^{13}$C-NMR: δ14.27, 20.57, 25.56, 25.64 (8C), 25.74 (2C), 26.66, 36.09, 55.48, 55.97, 91.09 (2C), 107.6, 127.0, 127.9, 128.1, 128.2, 128.3, 128.4, 128.6 (2C), 129.5, 132.1, 156.4 (2C), 159.9, 171.9.

Using docosahexaenoic acid (DHA) instead of EPA, the same steps as above were repeated to give N-(2,4,6-trimethoxyphenyl)-4,7,10,13,16,19-docosahexaenamide (Compound 2).

EI-MS (m/z): 493 ($M^+$)

Synthesis Example 2

Synthesis of N-(2,4,6-trifluorophenyl)-5,8,11,14,17-eicosapentaenamide (Compound 3)

Using EPA (1.21 g, 4 mmol), oxalyl chloride (0.761 g, 6 mmol) and anhydrous THF (5 ml), as well as 2,4,6-trifluoroaniline (529 mg, 4 mmol), $Et_3N$ (405 mg, 4 mmol) and anhydrous THF (3 ml), reactions were carried out according to the method of Synthesis Example 1. The concentrate obtained by concentrating washed AcOEt layer was applied to an $SiO_2$ column and purified with a hexane-AcOEt solvent to give the objective compound (927 mg, yield 53%). As a result of the TLC analysis [silica gel plate, developing solvent:hexane-AcOEt (8:2)], this compound showed a single spot by the detection with iodine and ultraviolet irradiation.

EI-MS (m/z): 431 ($M^+$)

$^1$H-NMR (400 MHz, $CDCl_3$): δ0.97 (t, J=7.5 Hz, 3H), 1.81 (m, J=7.2 Hz, 2H), 2.08 (m, J=7.5 Hz, 2H), 2.18 (m, J=6.3 Hz, 2H), 2.41 (t, J=6.9 Hz, 2H), 2.84 (m, 8H), 5.38 (m, 10H), 6.72 (t, J=3.2 Hz, 2H), 6.72 (bs, 1H).

$^{13}$C-NMR: δ14.27, 20.58, 25.28, 25.56, 25.66 (3C), 26.49, 35.56, 100.6 (2C), 110.5, 127.0, 127.9, 128.1, 128.21, 128.22, 128.3, 128.6, 128.9, 129.1, 132.1, 158.4, 161.0, 171.5.

Using docosahexaenoic acid (DHA) instead of EPA, the same steps as above were repeated to give N-(2,4,6-trifluorophenyl)-4,7,10,13,16,19-docosahexaenamide (Compound 4).

EI-MS (m/z): 457 ($M^+$)

Synthesis Example 3

Synthesis of N-(2,4,6-trimethylphenyl)-4,7,10,13, 16,19-docosahexaenamide (Compound 6)

Using DHA (95%, 1.31 g, 4 mmol), oxalyl chloride (0.761 g, 6 mmol) and anhydrous THF (5 ml), as well as 2,4,6- trimethylaniline (486 mg, 4 mmol), Et$_3$N (405 mg, 4 mmol) and anhydrous THF (3 ml), reactions were carried out according to the method of Synthesis Example 1. The concentrate obtained by concentrating washed AcOEt layer was applied to an SiO$_2$ column and purified with a hexane-AcOEt solvent to give the objective compound (1.35 g, yield 75%). As a result of the TLC analysis [silica gel plate, developing solvent:hexane-AcOEt (8:2)], this compound showed a single spot by the detection with iodine and ultraviolet irradiation.

EI-MS (m/z): 445 (M$^+$)

$^1$H-NMR (400 MHz, CDCl$_3$): δ0.97 (t, J=7.5 Hz, 3H), 2.07 (m, J=7.0, 7.6 Hz, 2H), 2.17 (s, 6H), 2.25 (s, 3H), 2.45 (m, 2H), 2.52 (m, 2H), 2.84 (m, 10H), 5.38 (m, 12H), 6.88 (s, 2H), 7.18 (bs, 1H).

$^{13}$C-NMR: δ14.3, 18.4 (2C), 20.6, 20.9, 25.56, 25.66 (3C), 25.72, 36.52, 127.0, 127.9, 128.0, 128.10, 128.12, 128.31, 128.32, 128.34, 128.4, 128.6, 128.9 (2C), 129.0, 129.6, 131.2 (2C), 135.2, 137.0, 170.9.

Using eicosapentaenoic acid (EPA) instead of DHA, the same steps as above were repeated to give N-(2,4,6-trimethylphenyl)-5,8,11,14,17-eicosapentaenamide (Compound 5).

EI-MS (m/z): 419 (M$^+$)

Synthesis Example 4

Synthesis of N-(2,6-dimethylphenyl)-5,8,11,14,17-eicosapentaenamide (Compound 7)

Using EPA (1.21 g, 4 mmol), oxalyl chloride (0.761 g, 6 mmol) and anhydrous THF (5 ml), as well as 2,6-dimethylphenylalanine (541 mg, 4 mmol), Et$_3$N (405 mg, 4 mmol) and anhydrous THF (3 ml), reactions were carried out according to the method of Synthesis Example 1. The concentrate obtained by concentrating washed AcOEt layer was applied to an SiO$_2$ column and purified with a hexane-AcOEt solvent to give the objective compound (1.34 g, yield 77%). As a result of the TLC analysis [silica gel plate, developing solvent:hexane-AcOEt (8:2)], this compound showed a single spot by the detection with iodine and ultraviolet irradiation.

EI-MS (m/z): 405 (M$^+$)

Using docosahexaenoic acid (DHA) instead of EPA, the same steps as above were repeated to give N-(2,6-dimethylphenyl)-4,7,10,13,16,19-docosahexaenamide (Compound 8).

EI-MS (m/z): 431 (M$^+$)

Synthesis Example 5

Synthesis of N-(2,6-diethylphenyl)-5,8,11,14,17-eicosapentaenamide (Compound 9)

Using EPA (1.21 g, 4 mmol), oxalyl chloride (0.761 g, 6 mmol) and anhydrous THF (5 ml), as well as 2,6-diethylphenylalanine (597 mg, 4 mmol), Et$_3$N (405 mg, 4 mmol) and anhydrous THF (3 ml), reactions were carried out according to the method of Synthesis Example 1. The concentrate obtained by concentrating washed AcOEt layer was applied to an SiO$_2$ column and purified with a hexane-AcOEt solvent to give the objective compound (1.34 g, yield 77%). As a result of the TLC analysis [silica gel plate, developing solvent:hexane-AcOEt (8:2)], this compound showed a single spot by the detection with iodine and ultraviolet irradiation.

EI-MS (m/z): 433 (M$^+$)

$^1$H-NMR (400 MHz, CDCl$_3$): δ0.97 (t, J=7.5 Hz, 3H), 1.19 (t, J=6.9 Hz, 6H), 1.85 (tt, J=7.21 Hz, 7.18 Hz, 2H), 2.08 (dq, J=7.0 Hz, 7.4 Hz, 2H), 2.21 (dt, J=7.3 Hz, 6.5 Hz, 2H), 2.42 (t, J=7.7 Hz, 2H), 2.59 (q, J=7.6 Hz, 4H), 2.85 (m, 8H), 5.38 (m, 10H), 7.11 (d, J=8.2 Hz, 2H), 7.21 (dd, J=8.2 Hz, 1H).

$^{13}$C-NMR: δ14.24, 14.39 (2C), 20.54, 24.83 (2C), 25.53, 25.62, 25.64, 25.66, 25.85, 26.87, 36.25, 126.29 (2C), 127.00, 127.65, 127.98, 128.03, 128.08, 128.19, 128.22, 128.29, 128.9, 129.03, 132.06 (2C), 132.59, 141.54 (2C), 171.8.

Using docosahexaenoic acid (DHA) instead of EPA, the same steps as above were repeated to give N-(2,6-diethylphenyl)-4,7,10,13,16,19-docosahexaenamide (Compound 10).

EI-MS (m/z): 459 (M$^+$)

Synthesis Example 6

Synthesis of N-(2,6-diisopropylphenyl)-4,7,10,13,16,19-docosahexaenamide (Compound 12)

Using DHA (1.31 g, 4 mmol), oxalyl chloride (0.761 g, 6 mmol) and anhydrous THF (5 ml), as well as 2,6-diisopropylaniline (709 mg, 4 mmol), Et$_3$N (405 mg, 4 mmol) and anhydrous THF (3 ml), reactions were carried out according to the method of Synthesis Example 1. The concentrate obtained by concentrating washed AcOEt layer was applied to an SiO$_2$ column and purified with a hexane-AcOEt solvent to give the objective compound (1.37 g, yield 70%). As a result of the TLC analysis [silica gel plate, developing solvent:hexane-AcOEt (8:2)], this compound showed a single spot by the detection with iodine and ultraviolet irradiation.

EI-MS (m/z): 487 (M$^+$)

$^1$H-NMR (400 MHz, CDCl$_3$): δ0.97 (t, J=7.5 Hz, 3H), 1.19 (d, J=6.8 Hz, 12H), 2.08 (td, J=7.6 Hz, 2H), 2.49 (m, 2H), 2.55 (t, 2H), 2.84 (m, 10H), 3.06 (qq, J=6.9 Hz, 2H), 5.38 (m, 12H), 7.17 (d, J=7.7 Hz, 2H), 7.29 (dd, J=7.7 Hz, 1H).

$^{13}$C-NMR: δ14.2, 14.4 (2C), 20.5, 24.8, 25.5, 25.62, 25.64, 25.66, 25.85, 26.87, 36.25, 126.29 (2C), 127, 127.7, 128.0, 128.2, 128.3, 128.9, 129.0, 132.1 (2C), 132.6, 141.5 (2C), 171.8.

Using eicosapentaenoic acid (EPA) instead of DHA, the same steps as above were repeated to give N-(2,6-diisopropylphenyl)-5,8,11,14,17-eicosapentaenamide (Compound 11).

EI-MS (m/z): 461 (M$^+$)

Preparative Example 1

Synthesis of N-5,8,11,14,17-eicosapentaenoyl ethylenediamine

EPA (not less than 95%, 3.03 g, 10 mmol) and N,N'-carbonyldiimidazole (1.78 g, 11 mmol) were dissolved in anhydrous THF (10 ml), and the mixture was reacted for about one hour at room temperature in a nitrogen stream. A solution of ethylene diamine (EDA, 1.5 g, 25 mmol) and triethylamine (2.55 g, 25 mmol) dissolved in anhydrous THF (10 ml) was added under ice cooling, and the mixture was allowed to react for 2 hours. After the completion of the reaction, 0.1N hydrochloric acid (60 ml) and chloroform-methanol (2:1, 300 ml) were added for partitioning. The lower layer was separated and concentrated under reduced pressure. The obtained concentrate was applied to a silica gel (160 g) column and eluted successively with chloroform-methanol-water (85:15:1, 1,000 ml) and chloroform-methanol-con. aqueous ammonia (85:15:1). The objective fractions were recovered from the obtained eluate fractions based on thin-layer chromatography (TLC) analysis as an index. The obtained fractions were concentrated to give the objective compound (2.72 g, yield 79%). As a result of the TLC analysis [silica gel plate, developing solvent:chloroform-methanol-water (75:25:2)], this compound showed a single spot by the detection with iodine, a 0.2% ninhydrin reagent and a 50% sulfuric acid-methanol reagent.
EI-MS (m/z): 344 ($M^+$)
$^1$H-NMR ($C_5D_5N$): δ0.7 (1H, m, H-9), 0.80 (3H, t, H-29), 0.90 (3H, d, H-27).

Preparative Example 2

Synthesis of N-4,7,10,13,16,19-docosahexaenoyl ethylenediamine

Docosahexaenoic acid (not less than 95%, 3.28 g, 10 mmol) and N,N'-carbonyldiimidazole (1.78 g, 11 mmol) were dissolved in anhydrous THF (10 ml), and the mixture was reacted for about one hour at room temperature in a nitrogen stream. A solution of ethylene diamine (EDA, 1.5 g, 25 mmol) and triethylamine (2.55 g, 25 mmol) dissolved in anhydrous THF (10 ml) was added under ice-cooling, and the mixture was allowed to react for 2 hours. After the completion of the reaction, 0.1N hydrochloric acid (60 ml) and chloroform-methanol (2:1, 300 ml) were added for partitioning. The lower layer was separated and concentrated under reduced pressure. The obtained concentrate was dissolved in a small amount of chloroform and applied to a silica gel (160 g) column activated with chloroform in advance, which was followed by elution with chloroform (500 ml), chloroform-methanol (98:2, 100 ml), chloroform-methanol-water (85:15:1, 1,000 ml) and chloroform-methanol-con. aqueous ammonia (85:15:1) in this order. The objective fractions were recovered from the obtained eluate fractions based on thin-layer chromatography (TLC) analysis as an index. The obtained fractions were concentrated to give the objective compound (2.86 g, yield 77.3%) as a pale-yellow oil. As a result of the TLC analysis [silica gel plate, developing solvent:chloroform-methanol-water (75:25:2)], this compound showed a single spot by the detection with iodine, a 0.2% ninhydrin reagent and a 50% sulfuric acid-methanol reagent.
EI-MS (m/z): 370 ($M^+$)
$^1$H-NMR ($C_5D_5N$): δ0.7 (1H, m, H-9), 0.80 (3H, t, H-29), 0.90 (3H, d, H-27).

Synthesis Example 7

Synthesis of N-(5,8,11,14,17-eicosapentaenoyl)-N'-(2,6-diisopropylanilinocarbonyl)ethylenediamine (Compound 13)

N-5,8,11,14,17-Eicosapentaenoyl ethylenediamine (737 mg, 2.14 mmol) was dissolved in $CHCl_3$ (5 ml), and 2,6-diisopropylphenyl isocyanate (435 mg, 2.14 mmol) was added. The mixture was reacted for about two hours while cooling in a nitrogen stream and concentrated under reduced pressure. The obtained concentrate was dissolved in a small amount of $CHCl_3$ and applied to $SiO_2$ (60 g) activated with $CHCl_3$ in advance, which was followed by elution with $CHCl_3$ (600 ml) and $CHCl_3$-MeOH-con. aqueous ammonia (95:5:0.5, 500 ml) in this order. The objective fractions were recovered from the obtained eluate fractions based on TLC analysis as an index. The obtained fractions were concentrated to give the objective compound (1.02 g, yield 87%).

The obtained compound was subjected to TLC analysis [silica gel plate, developing solvent:$CHCl_3$-MeOH-con. aqueous ammonia (95:5:0.5)]. As a result, a single spot was obtained by the detection with iodine and ultraviolet irradiation.
EI-MS (m/z): 547 ($M^+$)
$^1$H-NMR (400 MHz, $CDCl_3$): δ0.97 (t, J=7.5 Hz, 3H), 1.19 (s, 12H), 1.67 (m, 2H), 2.07 (m, J=7.5 Hz, 4H), 2.14 (m, 2H), 2.82 (m, 8H), 3.25 (m, 4H), 3.26 (m, 4H), 4.54 (bs, 1H), 5.37 (m, 10H), 6.06 (bs, 1H), 7.2 (d, J=7.6 Hz, 2H), 7.34 (t, J=7.6 Hz, 1H).
$^{13}$C-NMR: δ14.28, 20.57, 23.3 (2C), 24.3 (2C), 25.6 (5C), 26.77, 28.44 (2C), 36.09, 39.47, 41.68, 124.3 (2C), 127.1, 127.9, 128.1, 128.2, 128.3 (2C), 128.6, 128.7, 129.2 (2C), 130.5, 132.1, 147.6 (2C), 158.9, 173.4.

Using N-4,7,10,13,16,19-docosahexaenoyl ethylenediamine instead of N-5,8,11,14,17-eicosapentaenoyl ethylenediamine, the same steps as above were repeated to give N-(4,7,10,13,16,19-docosahexaenoyl)-N'-(2,6-diisopropylanilinocarbonyl)ethylenediamine (Compound 14).
EI-MS (m/z): 573 ($M^+$)

Synthesis Example 8

Synthesis of N-(4,7,10,13,16,19-docosahexaenoyl)-N'-(2,6-diisopropylanilinocarbonyl)piperazine (Compound 16)

DHA (1.64 g, 5 mmol) and CDI (972 mg, 6 mmol) were dissolved in anhydrous THF (10 ml), and the mixture was reacted for about 2 hours under cooling in a nitrogen stream. A solution of piperazine (861 mg, 10 mmol) and $Et_3N$ (1.02 g, 10 mmol) dissolved in anhydrous THF (30 ml) was added, and the mixture was allowed to react overnight. After the completion of the reaction, 0.1N hydrochloric acid (60 ml) and $CHCl_3$-MeOH (2:1, 300 ml) were added for partitioning. The lower layer was separated and concentrated under reduced pressure. The obtained concentrate was applied to an $SiO_2$ (100 g) column and eluted with $CHCl_3$ (500 ml), $CHCl_3$-MeOH (98:2, 800 ml) and $CHCl_3$-MeOH (95:5) in this order. The objective fractions were recovered from the obtained eluate fractions based on thin-layer chromatography (TLC) analysis as an index, and concentrated to give the objective compound (1.56 g, yield 78.9%).

This compound was subjected to TLC analysis [silica gel plate, developing solvent:$CHCl_3$-MeOH (95:5)]. As a result, a single spot was obtained by the detection with iodine. The obtained N-4,7,10,13,16,19-docosahexaenoylpiperazine (581 mg, 1.47 mmol) was dissolved in anhydrous THF (10 ml), and 2,6-diisopropylphenyl isocyanate (318 mg, 1.47 mmol) was added. The mixture was reacted for about 3 hours under cooling in a nitrogen stream and concentrated under reduced pressure. The obtained concentrate was dissolved in a small amount of $CHCl_3$ and applied to an $SiO_2$ (60 g) column activated with $CHCl_3$ in advance, which was followed by elution with $CHCl_3$ (600 ml) and $CHCl_3$-MeOH-con. aqueous ammonia (95:5:0.5, 500 ml) in this order. The objective fractions were recovered from the obtained eluate fractions based on TLC analysis as an index, and concentrated to give the objective compound (850 mg, yield 96%).

This compound was subjected to TLC analysis [silica gel plate, developing solvent:$CHCl_3$-MeOH-con. aqueous ammonia (90:10:1)]. As a result, a single spot was obtained by the detection with iodine and ultraviolet irradiation.
$^1$H-NMR (400 MHz, $CDCl_3$): δ0.98 (t, J=7.5 Hz, 3H), 1.19 (d, J=6.8 Hz, 12H), 2.08 (m, J=7.4 Hz, 7.5 Hz, 2H), 2.38 (m, 2H), 2.43 (m, 2H), 2.85 (m, 10H), 3.07 (dq, J=6.87 Hz, 2H), 3.44 (m, 6H), 3.65 (t, J=5.3 Hz, 2H), 5.39 (m, 12H), 7.16 (d, J=7.6 Hz, 2H), 7.27 (dd, J=7.7 Hz, 1H).

13C-NMR: δ14.24, 20.54, 22.93, 23.62 (4C), 25.53, 25.62 (2C), 25.64 (2C), 28.64 (2C), 33.04, 41.15, 43.78, 44.48, 45.28, 123.39 (2C), 127.01, 127.86, 127.93, 128.07, 128.08, 128.29, 128.33, 128.37, 128.58, 129.18 (2C), 132.04 (2C), 132.06, 146.49 (2C), 156.46, 171.34.

Using eicosapentaenoic acid (EPA) instead of DHA, the same steps as above were repeated to give N-(5,8,11,14,17-eicosapentaenoyl)-N'-(2,6-diisopropylanilinocarbonyl)piperazine (Compound 15).

1H-NMR (400 MHz, CDCl3): δ0.98 (t, J=7.5 Hz, 3H), 1.19 (d, J=6.7 Hz, 12H), 1.73 (m, J=6.8 Hz, 7.9 Hz, 7.5 Hz, 2H), 2.08 (qd, J=7.5 Hz, 7.2 Hz, 2H), 2.16 (td, J=6.8 Hz, 5.5 Hz, 2H), 2.32 (dd, J=7.9 Hz, 7.5 Hz, 2H), 2.84 (m, 8H), 3.07 (7th, J=6.7 Hz, 2H), 3.39 (m, 2H), 3.61 (m, 4H), 5.38 (m, 10H), 6.06 (s, 1H), 7.16 (dd, J=7.6, 1.8 Hz, 2H), 7.27 (t, J=7.6 Hz, 1H).

Synthesis Example 9

Synthesis of N-(5,8,11,14,17-eocosapentaenoyl)-N'-(2,6-diisopropylanilinocarbonyl)-1,2-diaminocyclohexane (Compound 17)

EPA (1.51 g, 5 mmol) and CDI (972 mg, 6 mmol) were dissolved in anhydrous THF (5 ml), and the mixture was reacted for about one hour under cooling in a nitrogen stream. A solution of 1,2-diaminocyclohexane (1.43 g, 12.5 mmol) and Et3N (1.27 g, 12.5 mmol) dissolved in anhydrous THF (5 ml) was added, and the mixture was reacted for about 2 hours. After the completion of the reaction, 0.1N hydrochloric acid (60 ml) and CHCl3-MeOH (2:1, 300 ml) were added for partitioning. The lower layer was separated and concentrated under reduced pressure. The obtained concentrate was applied to an SiO2 (80 g) column and eluted with CHCl3 (150 ml), CHCl3-MeOH (98:2, 400 ml) and CHCl3-MeOH-con. aqueous ammonia (90:10:1) in this order. The objective fractions were recovered from the obtained eluate fractions based on TLC analysis as an index, and concentrated to give the objective compound (1.79 g, yield 90%).

This compound was subjected to TLC analysis [silica gel plate, developing solvent:CHCl3-MeOH-con. aqueous ammonia (90:10:1)], and as a result, a single spot was obtained by the detection with iodine and a 0.2% ninhydrin reagent. The obtained N-5,8,11,14,17-eicosapentaenoyl-1,2-diaminocyclohexane (720 mg, 1.8 mmol) was dissolved in anhydrous THF (10 ml), and 2,6-diisopropylphenyl isocyanate (366 mg, 1.8 mmol) was added. The mixture was reacted for about 2 hours under cooling in a nitrogen stream, and concentrated under reduced pressure. The obtained concentrate was dissolved in a small amount of CHCl3 and applied to an SiO2 (100 g) column activated with CHCl3-MeOH-con. aqueous ammonia (98:2:0.25) in advance, which was followed by elution with the same solvent system. The objective fractions were recovered from the obtained eluate fractions based on TLC analysis as an index, and concentrated to give the objective compound (701 mg, yield 64.7%).

This compound was subjected to TLC analysis [silica gel plate, developing solvent:CHCl3-MeOH-con. aqueous ammonia (98:2:0.25)]. As a result, a single spot was obtained by the detection with iodine.

EI-MS (m/z): 601 (M+)

1H-NMR (400 MHz, CDCl3): δ0.97 (t, J=7.4 Hz, 3H), 1.08 (m, 1H), 1.17 (m, 12H), 1.27 (m, 2H), 1.67 (m, 4H), 1.82 (bd, 1H), 2.07 (m, J=7.4 Hz, 2H), 2.17 (m, 6H), 2.83 (m, 8H), 3.18 (bs, 2H), 3.33 (m, J=6.3 Hz, 1H), 3.64 (m, 1H), 4.12 (bs, 1H), 5.38 (m, 10H), 5.75 (bs, 1H), 6.68 (bd, J=6.3 Hz, 1H), 7.19 (d, J=7.7 Hz, 1H), 7.3 (t, J=7.7 Hz, 1H).

13C-NMR: δ14.29, 20.58, 23.25 (2C), 23.26, 24.00, 24.28 (2C), 25.15, 25.66 (2C), 25.72, 26.86, 28.52, 28.58 (2C), 32.45, 32.66, 36.45, 52.49, 56.02, 124.3 (2C), 127.1, 127.9, 128.2 (2C), 128.3, 128.4, 128.6 (2C), 129.3, 131.2, 132.0, 147.8 (2C), 158.3, 172.7.

Using docosahexaenoic acid (DHA) instead of EPA, the same steps as above were repeated to give N-(4,7,10,13,16,19-docosahexaenoyl)-N'-(2,6-diisopropylanilinocarbonyl)-1,2-diaminocyclohexane (Compound 18).

EI-MS (m/z): 627 (M+)

Synthesis Example 10

Synthesis of N-{4-(5,8,11,14,17-eicosapentaenoylamino)phenylmethyl}-N'-(2,6-diisopropylphenyl)urea (Compound 19)

EPA (1.21 g, 4 mmol) and CDI (778 mg, 4.8 mmol) were dissolved in anhydrous THF (5 ml), and the mixture was reacted for about one hour under cooling in a nitrogen stream. A solution of 4-aminobenzylamine (977 mg, 8 mmol) and Et3N (815 mg, 8 mmol) dissolved in anhydrous THF (5 ml) was added, and the mixture was reacted for about 2 hours. After the completion of the reaction, 0.1N hydrochloric acid (60 ml) and CHCl3-MeOH (2:1, 300 ml) were added for partitioning. The lower layer was separated and concentrated under reduced pressure. The obtained concentrate was applied to an SiO2 (80 g) column and eluted with CHCl3 (600 ml) and CHCl3-MeOH-H2O (90:10:1) in this order. The objective fractions were recovered from the obtained eluate fractions based on TLC analysis as an index, and concentrated to give the objective compound (1.46 g, yield 86%).

This compound was subjected to TLC analysis [silica gel plate, developing solvent:CHCl3-MeOH-H2O (90:10:1)]. As a result, a single spot was obtained by the detection with iodine and a 0.2% ninhydrin reagent. The obtained 4-(N-5,8,11,14,17-eicosapentaenoylamino)benzylamine (813 mg, 2 mmol) and Et3N (204 mg, 2 mmol) were dissolved in anhydrous THF (10 ml), and 2,6-diisopropylphenyl isocyanate (406 mg, 2 mmol) was added. The mixture was reacted for about 2 hours under cooling in a nitrogen stream, and concentrated under reduced pressure. The obtained concentrate was dissolved in a small amount of CHCl3 and applied to an SiO2 (800 g) column activated with CHCl3 in advance, which was followed by elution with CHCl3 (600 ml) and CHCl3-MeOH (98:2, 800 ml) in this order. The objective fractions were recovered from the obtained eluate fractions based on TLC analysis as an index, and concentrated to give the objective compound (1.07 g, yield 88%).

This compound was subjected to TLC analysis [silica gel plate, developing solvent:CHCl3-MeOH (98:2)]. As a result, a single spot was obtained by the detection with iodine and ultraviolet irradiation.

EI-MS (m/z): 609 (M+)

1H-NMR (400 MHz, CDCl3): δ0.97 (t, J=7.6 Hz, 3H), 1.14 (d, J=6.8 Hz, 12H), 1.79 (q, J=7.6 Hz, 2H), 2.07 (m, 2H), 2.16 (m, J=7.0 Hz, 2H), 2.33 (m, J=7.4 Hz, 7.7 Hz, 2H), 2.82 (m, 8H), 3.27 (m, J=6.8 Hz, 2H), 4.32 (d, J=5.8 Hz, 2H), 4.49 (bs, 1H), 5.36 (m, 10H), 5.95 (bs, 1H), 7.13 (dd, J=7.7 Hz, 8.3 Hz, 4H), 7.30 (t, J=7.7 Hz, 1H), 7.31 (bs, 1H), 7.41 (d, J=8.3 Hz, 2H).

13C-NMR: δ14.29, 20.58, 23.12 (2C), 24.45 (2C), 25.28, 25.57, 25.65, 25.67, 25.68, 26.63, 28.34 (2C), 36.96, 43.71, 119.9 (2C), 124.2 (2C), 127.0, 127.9, 128.1 (3C), 128.22 (2C), 128.3, 128.6 (2C), 129.1 (2C), 130.6, 132.1, 134.9, 137.2, 148.0 (2C), 157.6, 171.1.

Using docosahexaenoic acid (DHA) instead of EPA, the same steps as above were repeated to give N-{4-(4,7,10,13, 16,19-docosahexaenoylamino)phenylmethyl}-N'-(2,6-diisopropylphenyl)urea (Compound 20).
EI-MS (m/z): 635 (M⁺)

Synthesis Example 11

Synthesis of N-{4-(5,8,11,14,17-eicosapentaenoylaminomethyl)phenyl}-N'-(2,6-diisopropylphenyl)urea (Compound 21)

2,6-Diisopropylphenyl isocyanate (2.03 g, 10 mmol) and 4-aminobenzylamine (1.22 g, 10 mmol) were dissolved in anhydrous THF (10 ml). The mixture was reacted for about two hours at room temperature and concentrated under reduced pressure. The obtained concentrate was dissolved in a small amount of $CHCl_3$ and applied to an $SiO_2$ (150 g) column activated with $CHCl_3$ in advance, which was followed by elution with $CHCl_3$ (500 ml) and $CHCl_3$-MeOH-con. aqueous ammonia (90:10:1, 1,000 ml) in this order. The objective fractions were recovered from the obtained eluate fractions based on TLC analysis as an index, and concentrated to give the objective compound (3.1 g, yield 95%). This compound was subjected to TLC analysis [silica gel plate, developing solvent:$CHCl_3$-MeOH-con. aqueous ammonia (90:10:1)]. As a result, a single spot was obtained by the detection with iodine and a 0.2% ninhydrin reagent.

Eicosapentaenoic acid (EPA, 95%, 907 mg, 3 mmol) and oxalyl chloride (571 mg, 4.5 mmol) were dissolved in $CHCl_3$, and the mixture was reacted for about 2 hours while cooling in a nitrogen stream. The reaction mixture was concentrated under reduced pressure, and the concentrate and $Et_3N$ (265 mg, 2.6 mmol) were added to N-(4-aminomethylphenyl)-N'-( 2,6-diisopropylphenyl)urea (850 mg, 2.6 mmol) obtained above. Anhydrous THF (5 ml) was added and the mixture was reacted overnight while cooling in a nitrogen stream. The obtained reaction mixture was concentrated under reduced pressure and the concentrate was dissolved in a small amount of $CHCl_3$. The mixture was applied to an $SiO_2$ (120 g) column activated with $CHCl_3$ in advance, and eluted with $CHCl_3$ (600 ml) and $CHCl_3$-MeOH (98:2, 800 ml) in this order. The objective fractions were recovered from the obtained eluate fractions based on TLC analysis as an index and concentrated to give the objective compound (1.03 g, yield 65%). This compound was subjected to TLC analysis [silica gel plate, developing solvent:$CHCl_3$-MeOH (98:2)]. As a result, a single spot was obtained by the detection with iodine and ultraviolet irradiation.
EI-MS (m/z): 609 (M⁺)
¹H-NMR (400 MHz, $CDCl_3$): δ0.97 (t, J=7.5 Hz, 3H), 1.20 (bs, 12H), 1.71 (m, 2H), 2.07 (m, J=7.5 Hz, 2H), 2.11 (m, 2H), 2.18 (dd, J=7.4 Hz, 7.9 Hz, 2H), 2.81 (m, 8H), 3.32 (bs, 2H), 4.32 (d, J=5.5 Hz, 2H), 5.36 (m, 10H), 5.72 (bs, 1H), 6.00 (bs, 1H), 6.10 (bs, 1H), 7.11 (bs, 2H), 7.20 (bs, 2H), 7.25 (bs, 2H), 7.38 (bs, 1H).

Using docosahexaenoic acid (DHA) instead of EPA, the same steps as above were repeated to give N-{4-(4,7,10,13,16,19-docosahexaenoylaminomethyl)phenyl}-N'-(2,6-diisopropylphenyl)urea (Compound 22).
EI-MS (m/z): 635 (M⁺)

Experimental Example 1

Inhibitory activity against ACAT derived from human macrophage

Using, as an enzyme source, microsomal fractions prepared in the manner described below under Preparation of Microsome from U937 cells [human monocyte-derived cells known to differentiate into macrophages by the addition of TPA (12-O-tetradecanoylphorbol 13-acetate)] differentiated with TPA, the inhibitory activity against ACAT in the microsome fractions was determined as in the following. The compound of the present invention was dissolved in dimethyl sulfoxide and used as a sample solution. [1-¹⁴C] Oleoyl CoA (2 nmol/0.1 µCi/2 µl) dissolved in 10 mM sodium acetate solution (pH 6.0), oleoyl CoA (18 nmol/3 µl) dissolved in 10 mM sodium acetate (pH 6.0), sample solution (1 µl) and microsome (0.3 mg/10 µl) were added to 150 mM potassium phosphate buffer (pH 7.4, 184 µl) containing BSA (1.37 mg) and liposomes containing cholesterol wherein contained were cholesterol (5–6 µg) and phospholipid (24–25 µg), to the final volume of 200 µl, and the mixture was reacted at 37° C. for 30 minutes. Ethanol (1 ml) was added to stop the reaction, and n-hexane (4.5 ml) was added. The reaction mixture was centrifuged at 2,000 rpm for 2 minutes and the upper n-hexane layer was separated and recovered, whereby cholesterol oleate (reaction product) was extracted. n-Hexane was evaporated with a nitrogen gas and the residue was re-dissolved in n-hexane (50 µl), which was used as a sample for thin-layer chromatography. Cholesterol oleate (50 mg) was added to this sample and the mixture was spotted on silica gel G60 for TLC (Merk, Catalog No. 5554), which was followed by developing with a developing solvent of n-hexane:ether:methanol:acetic acid=170:40:2:2. After developing, the spot of cholesterol oleate was colored with iodine. The spot was cut out and dissolved in a xylene scintillator (Aquasol-2, Daiichi Pure Chemicals Co., Ltd.). The amount of cholesterol oleate was determined with a liquid scintillation counter. Then, the inhibitory activity [concentration necessary for inhibiting the production by 50% ($IC_{50}$)] was determined from the amount of cholesterol oleate. The results are shown in Table 1.

Preparation of Microsome

Human histiocyte lymphoma cells U937 were suspended in RPMI-1640 medium containing 10% fetal bovine serum and subcultured in a $CO_2$ incubator at 37° C. for the total of 31 generations. TPA was added to the final concentration of 0.1 µM by first preparing a solution of TPA (5 mM) in ethanol, diluting the same 500-fold to 10 µM with the medium (RPMI-1640), and adding this 10 µM solution in a proportion of 1/100 (for example, 1.5 ml was added when 150 ml of a culture solution was placed in a culture flask), and 24 hours later, the cells were scraped with a cell scraper. The cells thus scraped and the culture solution were centrifuged at 3,000 rpm for 5 minutes, and the cell fractions obtained as precipitate were once freezed at −70° C. and preserved. The cells preserved at −70° C. were thawed and homogenized at 4° C. in a Teflon homogenizer. The homogenate was centrifuged at 12,000 g for 15 minutes. The precipitate fractions containing nuclea and mitochondria were removed and the obtained supernatant was further centrifuged at 100,000 g for 60 minutes. The supernatant was discarded, and the obtained precipitate fractions were suspended in 150 mM potassium phosphate buffer (pH 7.4) and used as a microsomal fraction. The protein concentration of the microsome was calculated by the Lowry method [J. Biol. Chem., 193, pp. 265–275 (1951)].

Experimental Example 2

Inhibitory activity against ACAT derived from rat liver microsome

Using, as an enzyme source, the microsomal fractions prepared from rat liver in the manner described below under Preparation of Microsome, the inhibitory activity against ACAT in the microsome fractions was determined as in the following. The compound of the present invention was dissolved in dimethyl sulfoxide and used as a sample solution. [1-$^{14}$C] Oleoyl CoA (2 nmol/0.1 µCi/2 µl) dissolved in 10 mM sodium acetate solution (pH 6.0), oleoyl CoA (18 nmol/3 µl) dissolved in 10 mM sodium acetate (pH 6.0), sample solution (1 µl) and microsome (0.7 mg/10 µl) were added to 150 mM potassium phosphate buffer (pH 7.4, 184 µl) containing BSA (1.37 mg) and liposomes containing cholesterol wherein contained were cholesterol (5–6 µg) and phospholipid (24–25 µg), to the final volume of 200 µl, and the mixture was reacted at 37° C. for 30 minutes. Ethanol (1 ml) was added to stop the reaction, and n-hexane (4.5 ml) was added. The reaction mixture was centrifuged at 2,000 rpm for 2 minutes and the upper n-hexane layer was separated and recovered, whereby cholesterol oleate (reaction product) was extracted. n-Hexane was evaporated with a nitrogen gas and the residue was re-dissolved dissolved in n-hexane (50 µl), which was used as a sample for thin-layer chromatography. Cholesterol oleate (50 mg) was added to this sample and the mixture was spotted on silica gel G60 for TLC (Merk, Catalog No. 5554), which was followed by developing with a developing solvent of n-hexane:ether:methanol:acetic acid=170:40:2:2. After developing, the spot of cholesterol oleate was colored with iodine. The spot was cut out and dissolved in a xylene scintillator (Aquasol-2, Daiichi Pure Chemicals Co., Ltd.). The amount of cholesterol oleate was determined using a liquid scintillation counter. Then, the inhibitory activity [concentration necessary for inhibiting the production by 50% ($IC_{50}$)] was determined from the amount of cholesterol oleate. The results are shown in Table 1.

Preparation of Microsome

The liver was removed from a fasted rat and thoroughly perfused with 0.25M sucrose solution. The liver was weighed, minced with scissors or razor and placed in a Teflon homogenizer. The liver was homogenized with 9 volumes [9 ml per g (wet weight) of liver] of 0.25M sucrose solution or 50 mM Tris-HCl buffer (pH 7.5) containing 0.25M sucrose and 5 mM $MgCl_2$. The homogenate was centrifuged at 8,000–10,000 g for 10–15 minutes. The obtained supernatant was centrifuged at 105,000 g for 60–90 minutes. The sediment obtained from this centrifugation was suspended in 150 mM potassium phosphate buffer (pH 7.4) to give a microsomal fraction. The protein concentration of the microsome was calculated by the Lowry method [J. Biol. Chem., 193, pp. 265–275 (1951)].

TABLE 1

| | ACAT inhibitory activity | | |
|---|---|---|---|
| Test compound | $ACAT [IC_{50} (µM)]$ derived from human macrophage | $ACAT [IC_{50} (µM)]$ derived from rat liver | Selectivity |
| Compound 1 | 0.27 | 13.4 | 49.6 |
| Compound 2 | 0.50 | 20.3 | 40.6 |
| Compound 3 | 0.27 | >500 | >1852 |
| Compound 4 | 0.62 | >500 | >806 |
| Compound 5 | 0.90 | 43.1 | 47.9 |
| Compound 6 | 0.15 | >500 | >3333 |
| Compound 7 | 0.06 | 4.25 | 70.8 |
| Compound 8 | 0.28 | 73.9 | 264 |
| Compound 9 | 0.018 | 1.08 | 60 |
| Compound 10 | 0.029 | 11.45 | 395 |
| Compound 11 | 0.0097 | 2.4 | 247 |

TABLE 1-continued

| | ACAT inhibitory activity | | |
|---|---|---|---|
| Test compound | $ACAT [IC_{50} (µM)]$ derived from human macrophage | $ACAT [IC_{50} (µM)]$ derived from rat liver | Selectivity |
| Compound 12 | 0.0092 | 52.7 | 5728 |
| Compound 13 | 0.67 | >500 | >746 |
| Compound 14 | 4.52 | >500 | >111 |
| Compound 15 | 1.08 | >500 | >463 |
| Compound 16 | 0.69 | >500 | >725 |
| Compound 17 | 1.86 | >500 | >269 |
| Compound 18 | 2.63 | >500 | >190 |
| Compound 19 | 0.15 | >500 | >3333 |
| Compound 20 | 1.10 | 20.2 | 18.4 |
| Compound 21 | 6.64 | >500 | 75.3 |
| Compound 22 | 17.9 | >500 | 27.9 |

Note that the linoleoylamide derivative corresponding to Compound 1 and Compound 2 had $IC_{50}$ of 0.87 µM against ACAT derived from rat liver microsome, and that of 0.67 µM against ACAT derived from human macrophage, indicating scarce selectivity. The linoleoylamide derivative corresponding to Compound 7 and Compound 8 had $IC_{50}$ of 0.14 µM against ACAT derived from rat liver microsome, and that of 0.07 µM against ACAT derived from human macrophage, indicating only about twice greater selectivity. The linoleoylamide derivative corresponding to Compound 9 and Compound 10 which showed strong inhibitory activity had $IC_{50}$ of 0.10 µM against ACAT derived from rat liver microsome, and that of 0.02 µM against ACAT derived from human macrophage, indicating only about five times greater selectivity. The linoleoylamide derivative corresponding to Compound 11 and Compound 12 which showed the strongest inhibitory activity had $IC_{50}$ of 0.09 µM against ACAT derived from rat liver microsome, and that of 0.006 µM against ACAT derived from human macrophage, indicating only about fifteen times greater selectivity. The linoleoylamide derivative corresponding to Compound 15 and Compound 16 had $IC_{50}$ of not less than 500 µM against ACAT derived from rat liver microsome, and that of 4.61 µM against ACAT derived from human macrophage, indicating low activity.

Experimental Example 3

Reduction of cholesterol in blood of rats

Male slc:SD (SPF) rats (4 weeks of age weighing 70–90 g, Japan SLC Inc.) were randomly divided into 8 per group and bred for 3 days on a normal diet (solid diet for test animals, MF, manufactured by Oriental Yeast CO., LTD.). Then, the aforementioned diet supplemented with 5% cholesterol, 10% olive oil and 0.5% cholic acid was freely fed for 10 days. During the last five days, the test compound (Compounds 3–6, 8, 11 and 12) suspended in 0.5% aqueous methylcellulose solution was forcibly administered orally once a day in a dose of 10 ml/kg which contains 90 mg/kg/day of the test compound (total dose of the test compound being 450 mg/kg). The rats were fasted for 16 hours after the final administration and etherized. The blood was taken from the abdominal aorta, and serum was separated by centrifugation to determine the total cholesterol content in the serum. The control group was administered with 0.5% aqueous methylcellulose solution instead of the test compound suspended in 0.5% aqueous methylcellulose solution. The total cholesterol content was determined by an autoanalyzer (Hitachi 7150) according to the cholesterol oxidase.DAOS (DAOS:sodium N-ethyl-N-(2-hydroxy-3-sulfopropyl)-3,5-dimethoxyaniline (TC-V2, manufactured by Nippon Shoji Kaisha, Ltd.). The results are shown in Table 2. According to Table 2, the compound of the present invention showed marked cholesterol reduction.

TABLE 2

Reduction of cholesterol by the compound of the invention in cholesterol-loaded rats.

| Compound No. | %* |
|---|---|
| Compound 3 | 71 |
| Compound 4 | 59 |
| Compound 5 | 57 |
| Compound 6 | 68 |
| Compound 8 | 77 |
| Compound 11 | 78 |
| Compound 12 | 64 |

Note:
* is an average of 8 rats per group based on the cholesterol content in blood of control which was taken as 100%.

Experimental Example 4

Acute toxicity

Male slc:ICR mice (4 weeks of age, Japan SLC Inc.) were bred for 7 days on a normal diet (solid diet for test animals, Labo MR stock-SLC, manufactured by Japan SLC Inc.). Then, the mice were fasted for 16 hours and divided into 5 per group. The mice were forcibly administered orally with the test compound (Compounds 4, 5 and 9–12) dissolved in corn oil. The mice were further bred on a normal diet for 14 days to observe acute toxicity. As a result, the minimum lethal dose of the test compound was 2,000 mg/kg or above, thus demonstrating a very low toxicity of the compounds.

The compound of the present invention possesses not only high inhibitory activity against and high selectivity for ACAT derived from macrophage, but also decreasing action on cholesterol in blood. Accordingly, an ACAT inhibitor containing this compound is extremely useful as an agent for the prophylaxis and treatment of arteriosclerosis.

What is claimed is:
1. An aniline derivative of the formula (1)

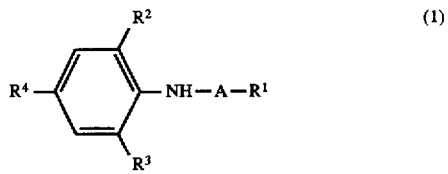

wherein $R^1$ is an eicosapentaenoyl or a docosahexaenoyl;

$R^2$ and $R^3$ are each independently an alkyl or alkoxy having 1 to 6 carbon atoms, or a halogen atom;

$R^4$ is a hydrogen atom, an alkyl or alkoxy having 1 to 6 carbon atoms, or a halogen atom; and A is a single bond, —C(=O)NH—(CH$_2$)$_n$—NH— wherein n is 2 or 3, or a bivalent group of the following formula

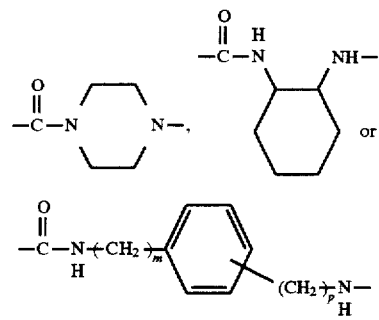

wherein m and p are each independently 0 or 1.

2. The aniline derivative of claim 1 having the following formula (1)

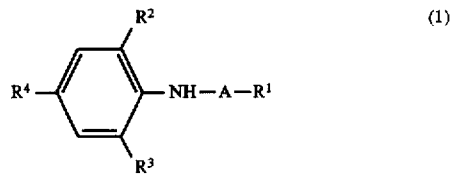

wherein $R^1$ is 5,8,11,14,17-eicosapentaenoyl or 4,7,10,13,16,19-docosahexaenoyl;

$R^2$ and $R^3$ are each independently a methyl, an ethyl, an isopropyl, a methoxy or a fluorine atom;

$R^4$ is a hydrogen atom, a methyl, a methoxy or a fluorine atom; and

A is a single bond, —C(=O)NH—(CH$_2$)$_2$—NH— or a bivalent group of the following formula

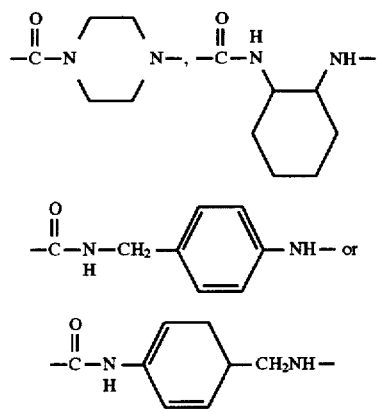

3. A pharmaceutical composition as an ACAT inhibitor or for the prophylaxis and treatment of arteriosclerosis comprising the aniline derivative of claim 1 and a pharmaceutically acceptable carrier.

4. A method of treating a patient having arteriosclerosis comprising administering to said patient a pharmaceutically effective amount of a compound of claim 1.

5. A method for prophylactically against arteriosclerosis comprising administering to a patient at risk of developing arteriosclerosis a prophylaxiscally effective amount of a compound of claim 1.

* * * * *

UNITED STATES PATENT AND TRADEMARK OFFICE
CERTIFICATE OF CORRECTION

PATENT NO. : 5,801,178
DATED : September 1, 1998
INVENTOR(S) : Yazawa et al.

It is certified that error appears in the above-identified patent and that said Letters Patent is hereby corrected as shown below:

ON THE TITLE PAGE:
Item [73]

Assignees: "Nippon Shoji Kaish Ltd." should read -- Nippon Shoji Kaisha Ltd. ---

" Sagami Chemical Research" should read -- Sagami Chemical Research Center --

Signed and Sealed this

Twenty-seventh Day of July, 1999

Attest:

Q. TODD DICKINSON

*Attesting Officer*    *Acting Commissioner of Patents and Trademarks*